United States Patent [19]

Kirchoff

[11] Patent Number: Plant 7,357

[45] Date of Patent: Oct. 16, 1990

[54] DAYLILY PLANT NAMED 'COLONEL SCARBOROUGH'

[75] Inventor: David Kirchoff, Sanford, Fla.

[73] Assignee: Jon Rackley, Eustis, Fla.

[21] Appl. No.: 390,894

[22] Filed: Aug. 8, 1989

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Roger L. Martin

[57] ABSTRACT

A new daylily plant having a distal leaf blade area of generally a yellow-green, olive-green and/or yellowish-green hue; the abaxial side having a distal blade area with an inconspicuously mottled, splotched basic field usually dominated by a yellow-green, olive-green and/or yellowish-green hue; spots and splotches generally lighter than that of the basic field but dominated by a yellow-green hue. Inflorescence shade is generally green, yellowish-green, olive-green and/or yellow-green hue; bracts being generally yellow-green hue and lighter in the basal and marginal areas. Branches of the corymb are dominated by a yellowish-green and/or yellow-green hue. The flower is very fragrant. Free portions of the petals are crispate-undulate in a narrow marginal band in the petal distal area; the distal area a basic field that is interrupted on the adaxial side, by a narrow axially extending stripe. Petal basal medial field and marginal areas, and basic field of the distal area, generally a greenish-yellow hue while the stripe is usually less intense than that of the basic field and dominated by a greenish-yellow, yellow-green and/or yellow hue; the basal area generally a greenish-yellow and/or yellow-green hue and usually lighter and less intense than in the medial field of the basal area. Specimens exhibit winter hardiness and heat resistance in Central Florida.

11 Drawing Sheets

BACKGROUND OF THE INVENTION

The invention relates to a new and distinct plant variety of the Liliaceae family and which has been named the *Hemerocaillis*×*lilioasphodelus* (cv) "Colonel Scarborough".

Most daylily varieties currently being grown for landscape bed planting purposes in the Central Florida Area have one or more growth habits which make their use in bed plantings less than desirable. Some varieties exhibit heat stress during the late summer months and go into a resting period or state of general plant declination. Other varieties lack winter hardiness and have foliage which is destroyed by the cold weather normally encountered in the Central Florida Area. Many varieties provide blooms which poorly exhibit the bloom color characteristics because of discontinuities in the bloom structure along the lateral edges of the sepals and petals. Most varieties provide no fragrance during anthesis. Many varieties suffer from frail bloom structures that permit normal wind movements to destroy their shapes before full maturity is realized.

SUMMARY OF THE INVENTION

A general object of the invention has been to develop a new daylily plant variety for use in landscape bed plantings in the Central Florida Area and which overcomes one or more of the undesirable growth habits referred to above.

The objective has been fully realized by the development of the new plant variety hereinafter described in detail. The new plant variety was developed in a nursery located at Sanford, Fla. in the Central Florida Area by pollinating the flower of a cultivar known as 'Little Jonie' with pollen from an unnamed hybrid of (cv) 'Frivilous Frills' and 'Robert Way Schlumpf'. The seeds from the pod of the mother plant were planted and grown under nursery conditions at the Sanford nursery and the seedling of the new plant variety described herein was selected by the inventor. Through successive propagations of cuttings initially taken from the mature plant developed from the selected seedling, it has been ascertained that specimens of the new plant variety are distinguishable from its antecedents and known related varieties by a growth habit which is evident in plant specimens of the new variety that have been propagated and grown under nursery conditions utilized in the growing of landscape bed plantings in the Central Florida Area, as combining the following principal characteristics:

(1) Leaves that (a) on the adaxial side have a distal blade area with a color which is usually dominated by a yellow green, olive green and/or yellowish green hue, and (b) on the abaxial side have a distal blade area with an inconspicuously mottled and splotched basic field which in color is usually dominated by a yellow green, olive green and/or yellowish green hue and in which the color of the spots and splotches is usually lighter than that of the basic field but also usually dominated by a yellow green hue.

(2) Leaves at maturity that (a) in length are usually 40 to 85 cm, (b) in width are usually 12 to 25 mm, and (c) in thickness are usually between 0.2 and 0.4 mm in the lamina intermediate the proximal and distal ends of the leaf.

(3) An inflorescence with compressed terete scapes which, at maturity, (a) are usually 30 and 55 cm in length, (b) are, in color, usually dominated by a green, yellowish green, olive green and/or yellow green hue, and (c) have scape bracts that, in color, are usually dominated by a yellow green hue and, in comparison to the center field areas of the bracts, usually tend to be lighter in the basal and marginal areas of the bracts.

(4) An inflorescence with a corymb which, at anthesis, (a) has branches that, in color, are usually dominated by a yellowish green and/or yellow green hue, (b) has bracts that, in color, are usually dominated by a yellow green hue and, in comparison to the center field areas of the bracts, usually tend to be lighter in the basal and marginal areas of the bracts, and (c) has pedicels that, in color, are usually dominated by a yellow green, yellowish green and/or green hue.

(5) An inflorescence with very fragrant flowers which, at anthesis, (a) have a homochlamydeous infundibular perianth with sepalous and petalous limbs that exhibit color fastness and overlap along the lateral margins, (b) the free portions of the sepals in the perianths usually being 90 to 120 mm in length and 35 to 40 mm in width, and, in color, usually being dominated by a greenish yellow and/or yellow green hue in the distal areas and medial fields of the basal areas thereof, (c) the free portions of the petals in the perianths being crispate-undulate in a narrow marginal band in the distal areas of the petal, usually being 90 to 115 mm in length and 50 to 70 mm in width, and having a distal area with a basic field that is interrupted, on the adaxial side, by a narrow axially extending stripe and further having a basal area with a medial field and marginal areas, the basic field of the distal area, in color, usually being dominated by a greenish yellow hue, the stripe, in color, usually being less intense than that of the basic field and dominated by a greenish yellow, yellow green and/or yellow hue, and the color in the basal area being usually dominated by a greenish yellow and/or yellow green hue and usually generally lighter and less intense than that in the medial field of the basal area.

(6) Plant specimens that exhibit winter hardiness in the sense that the specimens retain their leaves throughout the winter months normally encountered in the Central Florida Area and further exhibit excellent heat resistance in the sense that the specimens show no significant signs of heat stress during the late summer months encountered in the Central Florida Area.

BRIEF DESCRIPTION OF THE DRAWINGS

The accompanying drawings serve by color photographic means to illustrate the new plant variety and wherein: one sheet illustrates a potted specimen with a bloom about seven months following its propagation in the container; another sheet provides a view looking generally into the throat and along the axis of the bloom; yet another sheet provides a view looking into the throat of the same bloom but from a position that is offset from the axis thereof; still another sheet provides a bottom view of the bloom together with the corymb and some of the branches and bracts associated thereof; another sheet provides an enlargement of some of the buds, bracts, and branches seen in the last mentioned sheet; another sheet shows the bloom sepals as severed from the bloom, the sepal in the center of the illustration being viewed from its abaxial side whereas the other sepals are viewed from their adaxial sides; yet another sheet shows the bloom petals as severed from the bloom, the petal in the center of the illustration being viewed from its abaxial side whereas the other petals are viewed from their abaxial sides; another sheet shows a bloom as seen in a section taken generally along the axis of the bloom; another sheet shows an enlargement of the sectioned bloom as seen in the area of the ovary; yet another sheet shows the adaxial sides in the areas intermediate the distal and proximal ends of several leaves of a fan and; the last sheet shows the abaxial sides of the fan leaves shown in the last mentioned sheet.

DETAILED PLANT DESCRIPTION

The following is a detailed description of the new plant variety with colors and hues, unless otherwise clearly indicated by the text, as, for example, through the absence of color notations, being named in accord with the ISCC-NBS Method of Designating Colors (U.S. Dept. of Commerce, National Bureau of Standards, Circular 553), the named colors being interpreted from color notations derived by comparison with color specimens of the Munsell Book of Color.

The description is further based on observations of well fertilized plant specimens that were 5–8 months old from initial propagation as offshoots from mature plants. These plants were grown in full sun in a nursery at Eustis, Fla., U.S.A., wherein temperatures normally range from about 75° F. to about 105° F. during the summer months and from about 35° F. to about 80° F. during the winter months.

I. Name: *Hemerocallis* × *lilioasphodelus* (cv) "Colonel Scarborough".

II. Parentage:
- A. *Maternal.*—Hybrid (cv) 'Little Jonie'.
- B. *Paternal.*—An unnamed hybrid of (cv) 'Frivilous Frills' × 'Robert Way Schlumpf'.

III. Classification:
- A. *Botanic.*—(1) Family: Liliaceae or Lily. (2) Genus: *Hemerocallis.* (3) Species: × *Lilioasphodelus.*
- B. *Commercial.*—Daylily bedding plant.

IV. Form:
- A. *General.*—Terrestrial plant with fleshy tuberous roots producing fans of erect, distichous, keeled, linear leaves which become pendulous near the tips and which subtend a scapose, corymbose inflorescence during anthesis and with the plant forming additional fans by roots that spread and thus produce divisible propagations.
- B. *Fan size.*—(1) Width (at soil level): 2.5–4.0 cm. (2) Thickness (at soil level): 0.5–1.5 cm. (3) Greatest natural reach of leaves: Usually 50–80 cm. (4) Apogee of leaf arch (from ground level): 25–40 cm.
- C. *Number of fans.*—Usually 4–10 per propagation.
- D. *Number of leaves (living).*—Usually 3–17 per fan.

V. Stems:
- A. *General.*—Present only as several separate erect meristematic domes arising from a fleshy root and surrounded by overlapping, sheathing, distichous leaf bases, each having a latent axillary bud with potential to produce an inflorescence.
- B. *Stem texture.*—Fleshy.
- C. *Stem size.*—(1) Length: Usually 1–25 mm depending upon the age of the leafy fan. (2) Diameter: Usually 4–12 mm depending upon the age of the leafy fan.
- D. *Stem shape.*—Cylindric with conic tendencies.

VI. Leaves:
- A. *General.*—Simple and sessile with closely imbricate, undifferentiated, sharply keeled leaf bases and with the distal portions of the mature blades being reflexed.
- B. *Leaf texture.*—(1) Upper epidermis: Glabrous to weakly glaucescent and lacking hairs or scales. (2) Lower epidermis: Glabrous and smooth.
- C. *Leaf arrangement.*—Alternate, flabelliform and distichous.
- D. *Leaf margins.*—Plane and entire.

E. *Leaf venation.*—Parallel with a strong mid-vein, and otherwise obscure.

F. *Leaf shape.*—Linear from an undifferentiated keeled base and tapering to a narrow tip distally.

G. *Leaf size (at maturity).*—(1) Length: Usually 40 to 85 cm. (2) Width: Usually 12–25 mm intermediate the distal and proximal ends. (3) Thickness: Usually 0.2–0.4 mm in the lamina and usually 0.7–1.2 mm thick across the midvein intermediate the distal and proximal ends.

H. *Leaf color (at anthesis).*—(1) General: Adaxial side has a distal blade area with a color which is usually dominated by a yellow green, olive green and/or yellowish green hue and which merges proximally with the color in the basal blade area. The abaxial side has a distal blade area with an inconspicuously mottled and splotched basic field which in color is usually dominated by a yellow green, olive green, and/or yellowish green hue and in which the color of the spots and splotches is usually lighter and also dominated by a yellow green hue, the basic field color also merging proximally with the color in the basal blade area. (2) Distal blade area: (a) Adaxial side — Commonly moderate yellowish green (10 GY 5/6), dark yellowish green (10 GY 4/4) (2.5 G 4/4), moderate olive green (5 GY 4/4) (7.5 GY 4/4), moderate yellow green (5 GY 5/6) (7.5 GY 5/6) (7.5 GY 6/6) and/or strong yellow green (2.5 GY 6/8). (b) Abaxial side — Commonly strong yellow green (5 GY 5/8) (7.5 GY 5/8) (7.5 GY 6/8), moderate yellow green (5 GY 5/6) (5 GY 5/4) (7.5 GY 5/6) (7.5 GY 6/6), moderate olive green (5 GY 4/4) and/or dark yellowish green (10 GY 4/5) in the background of the basic field and pale yellow green (2.5 GY 9/2) (5 GY 9/2) and/or light yellow green (5 GY 8.5/6) (5 GY 9/4) (7.5 GY 9/4) in the spots and blotches. (3) Basal blade area: Commonly pale yellow green (7.5 GY 9/2) (2.5 GY 8/2) (near 2.5 GY 9/1) (near 5 GY 9/1) (5 GY 8.5/2), light yellow green (5 GY 8.5/6) (5 GY 9/4) (7.5 GY 9/4), yellowish white (near 2.5 GY 9/1) and/or greenish white (near 5 GY 9/1).

VII. Inflorescence:

A. *Form.*—(1) Generally erect with an elongate scape bearing appressed to somewhat distally spreading scape bracts below an elevated compound corymb comprised of a short axis bearing forked branches that ultimately terminate in buds which are progressively younger distally and on maturation respectively open to produce a single flower. (2) Number of flowers produced: 5–23 flowers per inflorescence with 1–4 blooms open at any one time and with a tendency for the number of flowers produced per inflorescence to be smaller towards the end of the season.

B. *Scape.*—(1) General: Terete to somewhat compressed, arising from a leaf axil and extending to the first branch at the base of the corymb, and with distally spreading, alternate scapebracts that have a spreading acute to acuminate tip and entire margins, and extending from the leaf axil to the first branch which delimits the base of the corymb. (2) Scape texture: Glabrous and fleshy. (3) Scape shape: Terete but compressed to become somewhat oval in cross section and tapering distally to the base of the corymb. (4) Scape size: (a) Length — Usually 30–55 cm from insertion to the lowermost branch of the corymb. (b) Diameter — Usually 8–18 mm along the major axis and 6–9 mm along the minor axis in the area of emergence from the leaf bases and usually 6–11 mm along the major axis and 4–6 mm along the minor axis at the base of the corymb. (5) Scape color: (a) General — Usually dominated by a green, yellowish green, olive green and/or yellow green hue. (b) Distal scape area — Commonly dark yellowish green (10 GY 4/4), moderate yellowish green (10 GY 5/6), moderate yellow green (7.5 GY 5/6) (7.5 GY 5/4) and/or strong yellow green (5 GY 5/8). (c) Proximal scape area — Commonly moderate yellow green (7.5 GY 5/4) (7.5 GY 5/6), moderate olive green (5 GY 4/4) (7.5 GY 4/4), dark yellowish green (10 GY 4/4) (2.5 G 4/4) (2.5 G 4/6), moderate yellowish green (10 GY 5/4) (10 GY 5/6) and/or moderate green (5 G 4/6).

C. *Scape bracts.*—(1) General: Sessile, simple, weakly carinate, transversely inserted, appressed below and spreading above, and located at internodal intervals of 5–20 cm between the lowermost scape-bract and the base of the corymb and 7–35 cm intervals between the origin of the scape and the proximal scape bract. (2) Scape bract texture: Chartaceous and glabrous. (3) Scape bract shape: Oblong lanceolate from a transverse line of insertion. (4) Scape bract margins: Plane, sometimes reflexed near the base and entire with a tendency to be membranous and slightly undulate-crisped distally. (5) Scape bract venation: Parallel and obscure. (6) Scape bract size (at anthesis): Usually 30–150 mm long and 8–20 mm wide with the most basal bract being the largest and the other scape-bracts becoming progressively smaller distally thereof and below the first inflorescence branch. (7) Scape bract color (at anthesis): (a) General — Usually dominated by a yellow green hue and tending to be lighter (higher Munsell value) in the basal and marginal areas. (b) Center field area — Commonly moderate yellow green (2.5 GY 5/6) (2.5 GY 6/6) (5 GY 5/6) (5 GY 6/6) and/or strong yellow green (5 GY 5/8) (5 GY 6/8) (7.5 GY 6/8). (c) Marginal blade area — Commonly pale yellow green (5 GY 9/2) (5 GY 8.5/2) (2.5 GY 9/2) (2.5 GY 8.5/2) and/or greenish white (5 GY 9/1). (d) Basal area — Commonly pale yellow green (2.5 GY 9/2) (5 GY 8/2) (5 GY 9/2) and/or light yellow green (2.5 GY 9/4) (5 GY 9/4).

D. *Corymb.*—(1) General: Comprises a series of terete axes that develop and grow from axillary buds of the corymb bracts to create a multiple dichasial branching system with the terminal branches being the pedicel for a single flower. (2) Primary inflorescence branches: (a) Primary branch number in corymb — Usually 2–5. (b) Primary branch texture — Glabrous and fleshy. (c) Primary branch shape — Terete or somewhat compressed terrete. (d) Primary branch size — 1. Length: Usually 10–60 cm from the first dichotomy to the next dichotomy distally thereof. 2. Diameter: Usually 3–5 mm intermediate the proximal and distal ends. (e) Primary branch color — Usually dominated by a yellowish green and/or yellow green hue and commonly dark yellowish green (10 GY 4/4), moderate yellowish green (10 GY 5/6), moderate yellow green (7.5 GY 5/6) (7.5 GY 5/4) and/or strong yellow green (5 GY 5/8). (3) Primary inflorescence bracts: (a) General — Sessile, simple, transversely inserted, erectopatent, and usually subtending a primary inflorescence branch or pedicel, or occasionally intermediate on a branch and lacking an axillary branch and usually being spaced apart at intervals of 10–60 mm. (b) Primary bract texture — Chartaceous and glabrous. (c) Primary bract shape — Ovate lanceolate, lanceolate to linear lanceolate, from a transverse line of insertion and tapered to an attenuated acuminate tip. (d) Primary bract margins — Generally plane and entire with crispate-undulate tendencies. (e) Primary bract venation — Parallel and obscure. (f) Primary bract size — Usually 30–40 mm long and 8–14 mm in maximum width. (g) Primary bract color (at anthesis) — 1. General: Usually dominated by a yellow green hue and tends to be lighter (higher Munsell value) in the marginal and basal areas. 2. Center field area: Commonly moderate yellow green (2.5 GY 5/6) (2.5 GY 6/6) (5 GY 5/6) (5 GY 6/6) (7.5 GY 5/6) and/or strong yellow green (5 GY 5/8) (5 GY 6/8) (7.5 GY 6/8). 3. Marginal area: Commonly pale yellow green (2.5 GY 9/2) (2.5 GY 8.5/2) (5 GY 8.5/2) (5 GY 9/2) and/or greenish white (5 GY 9/1). 4. Basal area: Commonly pale yellow green (2.5 GY 9/2) (5 GY 8/2) (5 GY 8.5/2) (5 GY 9/2) and/or light yellow green (2.5 GY 9/4) (5 GY 9/4). (4) Secondary inflorescence branches: (a) Secondary branch number in corymb — Usually 1–7. (b) Secondary branch texture — Glabrous and fleshy. (c) Secondary branch shape — Terete or somewhat compressed terrete. (d) Secondary branch size — 1. Length: Usually 5–40 mm from the second dichotomy to the next dichotomy distally thereof. 2. Diameter: Usually 2–4 mm (maximum) intermediate the proximal and distal ends. (e) Secondary branch color — Usually dominated by a yellowish green and/or yellow green hue, and commonly dark yellowish green (10 GY 4/4), moderate yellowish green (10 GY 5/6), moderate yellow green (5 GY 5/6) (5 GY 5/4) (7.5 GY 5/6) (7.5 GY 5/4) and/or strong yellow green (5 GY 5/8) (2.5 GY 6/8). (5) Secondary inflorescence bracts: (a) General — Sessile, simple, transversely inserted, erectopatent, usually subtending a secondary inflorescence branch or pedicel or occasionally intermediate on the branch and spaced apart at intervals of 5–40 mm. (b) Secondary bract texture — Chartaceous and glabrous. (c) Secondary bract shape — Oblong lanceolate, ovate or ovate lanceolate, from a transverse line of insertion and with an acuminate to acute tip. (d) Secondary bract margins — Generally plane and entire with crispate-undulate tendencies. (e) Secondary bract venation — Parallel and obscure. (f) Secondary bract size — Usually 10–30 mm long and 5–10 mm in maximum width. (g) Secondary bract color (at anthesis) — 1. General: Usually dominated by a yellow green hue and tending to be lighter (higher Munsell value) in the marginal and basal areas. 2. Center blade area: Commonly moderate yellow green (2.5 GY 5/6) (2.5 GY 6/6) (5 GY 5/6) (5 GY 6/6) (5 GY 7/6), light yellow green (2.5 GY 8/6) (2.5 GY 8.5/6) (5 GY 8/6) (5 GY 8.5/6) (5 GY 9/6), brilliant yellow green (5 GY 8.5/8) and/or strong yellow green (5 GY 5/8) (5 GY 6/8) (7.5 GY 5/8) (7.5 GY 6/8). 3. Marginal area: Commonly pale yellow green (2.5 GY 9/2) (2.5 GY 8.5/2) (5 GY 8.5/2) (5 GY 9/2) and/or greenish white (5 GY 9/1). 4. Basal area: Commonly pale yellow green (2.5 GY 9/2) (5 GY 8/2) (5 GY 8.5/2) (5 GY 9/2) and/or light yellow green (2.5 GY 8/6) (2.5 GY 8.5/6) (5 GY 8/6) (5 GY 8.5/6). (6) Tertiary inflorescence branches: (a) Tertiary branch number in corymb — Usually 0–6. (b) Tertiary branch texture — Glabrous and fleshy. (c) Tertiary branch shape — Usually compressed terete. (d) Tertiary branch size — 1. Length: Usually 4–18 mm from the third dichotomy, when present. 2. Diameter: Usually 2–4 mm maximum intermediate the proximal and distal ends. (e) Tertiary branch color — Usually dominated by a yellowish green and/or yellow green hue and commonly dark yellowish green (10 GY 4/4), moderate yellowish green (10 GY 5/6), moderate yellow green (5 GY 5/6) (5 GY 5/4) (7.5 GY 5/6) (7.5 GY 5/4) and/or strong yellow green (5 GY 5/8) (2.5 GY 6/8). (7) Tertiary inflorescence bracts: (a) General — Sessile, simple, transversely inserted, erectopatent, usually subtending a tertiary branch or a pedicel, or occasionally intermediate on the branch and spaced apart at intervals of 3–15 mm. (b) Tertiary bract texture — Chartaceous and glabrous. (c) Tertiary bract shape — Oblong lanceolate, ovate lanceolate, ovate to broadly ovate from a transverse line of insertion and with an acuminate to acute tip. (d) Tertiary bract margins — Generally plane and entire with crispate-undulate tendencies. (e) Tertiary bract venation — Parallel and obscure. (f) Tertiary bract size — Usually 7–20 mm long and 3–6 mm in maximum width. (g) Tertiary bract color (at anthesis) — 1. General: Usually dominated by a yellow green hue and tends to be lighter (higher Munsell value) in the marginal and basal areas. 2. Center blade area: Commonly light yellow green (2.5 GY 8/6) (2.5 GY 8.5/6) (2.5 GY 8.5/4) (2.5 GY 9/4) (5 GY 9/4) (5 GY 8/6) (5 GY 8.5/6), brilliant yellow green (2.5 GY 9/8) (2.5 GY 8.5/8) (2.5 GY 8.5/10) d(5 GY 8.5/8), moderate yellow green (2.5 GY 7/6) (2.5 GY 6/6) (5 GY 5/6) (5 GY 6/6) (5 GY 7/6) and/or strong yellow green (5 GY 5/8) (5 GY 6/8) (7.5 GY 5/8) (7.5 GY 6/8). 3. Marginal area: Commonly pale yellow green (2.5 GY 9/2) (2.5 GY 8.5/2) (5 GY 8.5/2) (5 GY 9/2) and/or greenish white (5 GY 9/1). 4. Basal area: Commonly pale yellow green (2.5 GY 9/2) (5 GY 8/2) (5 GY 8.5/2) (5 GY 9/2) and/or light yellow green (2.5 GY 8/6) (2.5 GY 8.5/6) (5 GY 8/6) (5 GY 8.5/6). (8) Pedicels: (a) Pedicel texture — Glabrous and fleshy. (b) Pedicel shape — Usually terete and expanding distally to the base of the flower. (c) Pedicel size — 1. Length: Usually 7–10 mm long, as measured from the nearest subtending bract. 2. Diameter: Usually 2.5–3.0 mm intermediate the proximal and distal ends and 3.0–4.5 mm at the distal end. (d) Pedicel color — Usually dominated by a yellow green, yellowish green and/or green hue and commonly moderate yellow green (7.5 GY 5/6) (7.5 GY 5/4), moderate yellowish green (10 GY 5/4) (10 GY 5/6), dark yellowish green (10 GY 4/4) (2.5 GY 4/4) (2.5 GY 4/6) and/or moderate green (5 GY 4/6).

*E. Flowers.*—(1) General: Complete, hypogynous, actinomorphic and perfect (bisexual) with a basially fused perianth that has dimorphic tepals comprised of three petals and three sepals which are narrower than the petals, an androecium of six curved stamens, and a gynoecium which has a tricarpellate superior ovary with axile placentation bearing numerous whitish ovules, a curved slender terete style and a small capitate and weakly tri-lobed stigma. Sometimes a tetra merous flower will be formed near the end of the flowering season although this is a rare occurrence. (2) Perianth: (a) General — Comprised of six tepals fused to form a perianth tube which becomes limbate distally with three expanded spreading sepals alternate to three broadly expanded petals. (b) Sepals — 1. General: Inserted on the receptacle below the ovary and fused with the petals to form a perianth tube and separating into free limbs and spreading from the distal end of the tube. 2. Sepal texture (free portion): Glabrous and fleshy. 3. Sepal shape (free portion): Elliptic to oblong elliptic distal to the perianth tube and with an obtuse, sometimes cucullate tip. 4. Sepal margins (free portion): Generally plane and entire with crispate-undulate tendencies. 5. Sepal venation (free portion): Usually parallel with an occasional dichotomously branched vein. 6. Sepal size (free portion): Usually 90–120 mm long and 35–40 mm maximum width for the limb of the calyx. 7. Sepal color (free portion): a. General — A distal area which in color is usually dominated by a greenish yellow and/or yellow green hue and a basal area with a medial field that is usually dominated by a greenish yellow and/or yellow green hue. b. Distal area (distal ⅔rd of free sepal) — Commonly light greenish yellow (near 10 Y 8.5/8) (near 10 Y 8/8) (10 Y 9/6) (near 10 Y 9/8) (10 Y 8.5/6) (7.5 Y 9/6) (near 7.5 Y 8.5/8) (near 7.5 Y 9/8), pale greenish yellow (10 Y 9/4) (7.5 Y 9/4), moderate greenish yellow (near 10 Y 8/8) (near 10 Y 7/8), strong greenish yellow (near 10 Y 8/8) (near 10 Y 7/8), brilliant greenish yellow (10 Y 8.5/8) (near 10 Y 8/8) (near 10 Y 9/8) (near 7.5 Y 8/8) (7.5 Y 8.5/10) (near 7.5 Y 9/8) (2.5 GY 8.5/8) (2.5 GY 8.5/10). c. Basal area (proximal ⅓rd of free sepal) — (1) Medial Field: Commonly light greenish yellow (10 Y 8.5/6) (near 10 Y 8/6), moderate greenish yellow (near 10 Y 8/6), light yellow green (2.5 GY 8.5/6) (5 GY 8.5/6), brilliant yellow green (2.5 GY 8/8) (2.5 GY 8.5/8) (5 GY 8/8) and/or strong yellow green (2.5 GY 7/8). (2) Marginal Areas: Commonly pale yellow green (10 Y 9/2) (2.5 GY 9/2), pale greenish yellow (10 Y 9/4), pale yellow (near 7.5 Y 9/2) (near 5 Y 9/2) and/or yellowish white (near 7.5 Y 9/2) (near 5 Y 9/2). (c) Petals — 1. General: Inserted on the receptacle below the ovary and fused with sepals to form a perianth tube and separating into free limbs and spreading from the distal end of the tube. 2. Petal texture (free portion): Glabrous and fleshy. 3. Petal shape (free portion): Broadly elliptic to obovate distal to the perianth tube and with a broadly rounded, obtuse tip. 4. Petal margins (free portion): Generally plane and entire in the lower one-third of the petal limb and becoming crispate-undulate distally in a narrow marginal band approximately one-tenth the maximum width of the petal. 5. Petal venation (free portion): Usually parallel below with veins commonly once dichotomously branched in the distal portion of the petal. 6. Petal size (free portion): Usually 90–115 mm long and 50–70 mm maximum width in the free portion of the corolla. 7. Petal color (free portion): a. General — A distal area with a basic field which in color is usually dominated by a greenish yellow hue and which, on the adaxial side, has a narrow axially extending stripe that in color is generally less intense (lower Munsell chroma) than the surrounding color and dominated by a greenish yellow, yellow green and/or yellow hue, and a basal area with a medial field and marginal areas, the color in the basal area being usually dominated by a greenish yellow and/or yellow green hue and the color in the marginal areas usually being generally lighter (higher Munsell value) and less intense (lower Munsell chroma) than that in the medial field. b. Distal area (distal ⅔rd of free petal) — (1) Basic field: Commonly pale greenish yellow (7.5 Y 9/4) (10 Y 9/4), light greenish yellow (7.5 Y 9/6) (10 Y 9/6) (near 7.5 Y 9/8) (near 10 Y 9/8) and/or brilliant greenish yellow (near 7.5 Y 9/8) (near 10 Y 9/8) (10 Y 9/10). (2) Axial stripe (adaxial side): Commonly pale yellow green (10 Y 9/2), pale greenish yellow (10 Y 9/4), pale yellow (near 7.5 Y 9/2) and/or yellowish white (near 7.5 Y 9/2). c. Basal area — (1) Medial field: Commonly light greenish yellow (10 Y 8.5/6) (near 10 Y 8.5/8) (near 10 Y 8/6) (near 10 Y 8/8), moderate greenish yellow (near 10 Y 8/8) (near 10 Y 8/6), strong greenish yellow (near 10 Y 8/8) (near 10 Y 8/10), brilliant greenish yellow (near 10 Y 8/8) (near 10 Y 8/10) (near 10 Y 8.5/8) (near 10 Y 8.5/10), strong yellow green (2.5 GY 7/8) and/or brilliant yellow green (2.5 GY 8/8) (2.5 GY 8.5/8) (2.5 GY 9/8). (2) Marginal area: Commonly pale greenish yellow (10 Y 9/4), pale yellow green (10 Y 9/2) (2.5 GY 9/2) and/or light yellow green (2.5 GY 9/4). (d) Perianth tube (at anthesis) — 1. General: Inserted on the receptacle below the ovary and comprised of fused sepal and petal bases, the tube extending from the receptacle to the region of separation of the floral parts. 2. Perianth tube texture: Glabrous and fleshy. 3. Perianth tube shape: Cylindrical and hollow with a slight bulbous expansion near the base. 4. Perianth tube size: a. Length — Usually 20–30 mm long. b. Outside diameter — Usually 6–9 mm in the basal region and 5–7 mm intermediate the proximal and distal ends. c. Inside diameter: Usually 2.5–4.0 mm intermediate the proximal and distal ends. 5. Perianth tube color: a. General — Usually dominated by a yellow green hue on the exterior side and usually dominated by a yellow green and/or greenish yellow hue on the interior side. b. Exterior side — Commonly strong yellow green (2.5 GY 7/8) (2.5 GY 7/10) and brilliant yellow green (2.5 GY 8/10) (2.5 GY 8/8). c. Interior side — Commonly pale yellow green (2.5 GY 9/2) (10 Y 9/2), light yellow green (2.5 GY 9/4) and/or pale greenish yellow (10 Y 9/4). (e) Stamens — 1. General: Inserted on the perianth at the top of the perianth tube with the filaments curved downwardly and then upwardly to place the anthers in direct alignment with the perianth tube and with the dehiscent face of the anthers facing the perianth tube and ending well below the end of the long and similarly curved style. 2. Stamen texture: Glabrous and fleshy for the filaments and chartaceous for dehiscing anthers. 3. Stamen shape: Terete, elongated and curved for the filaments and bi-lobed cylindric for the unopened anthers. 4. Stamen size: a. Filaments — (1) Length: Usually 60–75 mm. (2) Diameter: Usually 2.5–3.5 mm at the proximal end, 1.5–3.0 mm intermediate the proximal and distal ends, and 1.0–2.0 mm at the distal end. b. Anthers — (1) Length: Usually 9–13 mm. (2) Diameter (maximum): Usually 1.5–3.0 mm. 5. Stamen color: a. Filaments — Usually dominated by a greenish yellow hue and commonly light greenish yellow (near 7.5 Y 8.5/8) (7.5 Y 9/6) (10 Y 9/6) (near 7.5 Y 9/8) (near 10 Y 9/8) (near 10 Y 8.5/8) and/or brilliant greenish yellow (near 7.5 Y 8.5/8) (near 7.5 Y 9/8) (near 10 Y 9/8) (near 10 Y 8.5/8) (10 Y 8.5/10) with tendencies for the distal portion to be lighter (higher Munsell value) and less intense (lower Munsell croma) than the proximal portion. b. Anther connective — Color usually dominated by a yellowish pink hue and commonly pale yellowish pink (near 2.5 YR 8/2) (near 5 YR 8/2), grayish yellowish pink (near 2.5 YR 8/2) (near 5 YR 8/2), brownish pink (near 5 YR 8/2), light yellowish pink (near 2.5 YR 8/4) and/or moderate yellowish pink (near 2.5 YR 8/4). c. Pollen (open anthers) — Usually dominated by an orange yellow hue and commonly light orange yellow (near 7.5 YR 8/10), moderate orange yellow (near 7.5 YR 7/10) (near 7.5 YR 8/10), strong orange yellow (7.5 YR 7/12) (near 7.5 YR 7/10) (near 7.5 YR 8/10) (10 YR 7/12) and/or brilliant orange yellow (near 7.5 YR 8/10). (f) Pistil — 1. General: Inserted on the receptacle and having a truncated conic ovary indistinctly six-lobed and bearing a single, terete, helically grooved (at 10× magnification), curved style which terminates at a constriction subtending an inconspicuous discoid and weakly tripartite stigma component. 2. Ovary: a. Ovary texture — Glabrous and fleshy. b. Ovary shape — Conic with a truncated apex bearing the style and with three shallow, rounded and longitudinally oriented external sulci and containing inside six rows of ovules in 4–7 tiers. c. Ovary size — Usually 4–7 mm high and 3–5 mm in maximum diameter with enclosed ovules being 0.2–0.3 mm in maximum diameter. d. Ovary color — Usually dominated by a yellow green hue and commonly light yellow green (2.5 GY 8.5/6), moderate yellow green (5 GY 7/6), strong yellow green (2.5 GY 7/8) (2.5 GY 7/10) (5 GY 7/8) (5 GY 7/10) and/or brilliant yellow green (2.5 GY 8.5/8) (2.5 GY 8/8) (5 GY 8/8). The ovules are commonly yellowish white (10 Y 9/1). 3. Style: a. Style texture — Glabrous and fleshy. b. Style shape — Terete with three shallow helical external grooves (at 10× magnification). c. Style size — Usually 120–150 mm long and 1–2 mm in diameter intermediate the proximal and distal ends. d. Style color — Commonly pale greenish yellow (10 Y 8.5/4) (10 Y 9/4), light greenish yellow (10 Y 8.5/6), pale yellow (near 7.5 Y 9/2) and/or yellowish white (near 7.5 Y 9/2). 4. Stigma: a. Stigma texture — Bullate and fleshy. b. Stigma shape — Discoid, weakly tripartite and with a minute triangular central pore. c. Stigma size — Usually about 1 mm in diameter and 0.2–0.3 mm thick. d. Stigma color — Commonly pale yellow (near 7.5 Y 9/2) and/or yellowish white (near 7.5 Y 9/2).

VIII. Other growth habits:

A. *Foliage.*—(1) The new plant variety has a generally darker foliage color than most other varieties currently being grown in Central Florida for landscape bed planting purposes. (2) The leaf blades of the new plant variety are generally broader than most other varieties currently being grown in Central Florida for landscape bed planting purposes. (3) The new plant variety has a graceful mounding habit with the new leaves emerging vertically and thereafter arching over to form a graceful mound or clump. (4) The new plant variety is a stout, vigorous and strong growing variety that (a) exhibits winter hardiness in the sense that the variety retains its foliage throughout the winter months normally encountered in the Central Florida Area, and (b) exhibits excellent heat resistance in the sense that the variety shows no significant symptoms of heat stress in the late summer months encountered in the Central Florida Area.

B. *Flower.*—(1) The new plant variety produces a generally larger flower than most other varieties grown in the Central Florida Area for landscape bed planting purposes. (2) The new plant variety produces a flower form which because of the substantial width dimensions of the mature sepals and petals has no side edge discontinuities that detract from the color of the bloom in view. (3) The new plant variety produces relatively thick sepals and petals that resist appreciable damage from normal wind movements of the plant parts. (4) The new plant variety exhibits a color fastness that resists bloom color fading in the afternoon of anthesis. (5) The new plant variety has a pronounced fragrance.

C. *Scapes.*—(1) The new plant variety produces upright and stout scapes that support the flowers well above the foliage. (2) The new plant variety produces scapes that mature blooms in the middle of the daylily blooming season in the Central Florida Area and has the tendency to emerge new scapes after the initial thrust of the scapes during the blooming season to, in effect, lengthen the duration of the blooming period.

GENERAL DESCRIPTION OF A PLANT SPECIMEN

The following is a general description of a specimen of the new plant variety that was grown in a nursery at Eustis, Fla. from a single fan separated by vegetative division of a single plant clump, the description having been taken during the period of flowering and during the month of June.

Age of plant: Approximately eight months from initial propagation of a single fan of indeterminable age.

Plant height: 60 cm to the top of the tallest inflorescence and 35 cm to the apogee of the arcuate leaves.

Largest single fan:

I. *Width of fan at soil level.*—3 cm.

II. *Thickness of fan at soil level.*—0.9 cm.

III. *Greatest natural reach of leaves.*—60 cm.

Number of fans: 6.

Leaves:

I. *Number of leaves.*—41 in 6 fans with a range of 5–10 per fan in the specimen.

II. *Leaf length.*—Ranges from 45–64 cm for mature leaves.

III. *Leaf width.*—Ranges from 13–21 mm intermediate the proximal and distal ends.

IV. *Leaf thickness.*—Ranges from 0.25–0.35 mm in the lamina and 0.9–1.1 at the midvein intermediate the distal and proximal ends.

V. *Leaf color (at anthesis).*—A. Distal blade area — (1) Adaxial side: Dark yellowish green (10 GY 4/4), moderate yellowish green (10 GY 5/6), moderate olive green (7.5 GY 4/4) and moderate yellow green (7.5 GY 5/6). (2) Abaxial side: Moderate yellow green (5 GY 5/6) and strong yellow green (5 GY 5/8) (7.5 GY 5/8) (7.5 GY 6/8) in the background of the basic field and pale yellow green (2.5 GY 9/2) (5 GY 9/2) and light yellow green (5 GY 9/4) in the spots and blotches. B. Basal blade area — Light yellow green (5 GY 8.5/6) (5 GY 9/4) (7.5 GY 9/4), pale yellow green (7.5 GY 9/2) (5 GY 8.5/2) (2.5 GY 8/2), yellowish white (near 2.5 GY 9/1) and greenish white (near 5 GY 9/1).

Inflorescence:

I. *Number of inflorescences.*—A. Inflorescence phenology — Two (2) with open flowers and unopened buds, one (1) green scape but past flowering and with no remaining buds, and one (1) dead scape past flowering. B. Flowers produced per inflorescence — (1) Dead scape (No. 1): 21. (2) Green scape (past flowering) (No. 2): 10. (3) Flowering inflorescence (No. 3): 10 including one (1) bud and two (2) open flowers. (4) Flowering inflorescence (No. 4): 6 including three (3) buds and one (1) open flower.

II. *Scape.*—A. General — (1) Scape size (at anthesis): (a) Length (to the corymb) — No. 1: 40 cm. No. 2: 44.5 cm. No. 3: 38.5 cm. No. 4: 39.5 cm. (b) Diameter (major axis×minor axis) — (1) At emergence of the scape from the leaves: No. 1: 15×8 mm. No. 2: 18×9 mm. No. 3: 13×6.5 mm. No. 4: 14×7 mm. (2) Near the base of the corymb: No. 1: 10×4 mm. No. 2: 8×5 mm. No. 3: 7.5×5 mm. No. 4: 9×5 mm. (2) Scape color (at anthesis): (a) Distal scape area — Dark yellowish green (10 GY 4/4), moderate yellowish green (10 GY 5/6) and moderate yellow green (7.5 GY 5/4) (7.5 GY 5/6). (b) Proximal scape area — Moderate yellow green (7.5 GY 5/4) (7.5 GY 5/6), moderate yellowish green (10 GY 5/6), dark yellowish green (10 GY 4/4) and moderate green (5 GY 4/6). B. Scape bracts — (1) Number of bracts: No. 1: 3. No. 2: 4. No. 3: 3. No. 4: 3. (2) Distance between bracts (commencing from proximate end of scape): No. 1: 10, 8 and 11.5 cm respectively. No. 2: 20.5, 6, 7 and 5 cm respectively. No. 3: 31, 2, 11.5 cm respectively. No. 4: 11, 11 and 18 cm respectively. (3) Scape bract sizes (flowering inflorescences with live bracts): (a) Length (commencing from the proximal end) — No. 3: 70, 48 and 35 mm respectively. No. 4: 43, 35 and 32 mm respectively. (b) Maximum width (commencing from the proximal end) — No. 3: 18, 13 and 13 mm respectively. No. 4: 13, 12 and 13 mm respectively. (4) Scape bract color (at anthesis): (a) Center field area — Strong yellow green (5 GY 5/8) (5 GY 6/8) (7.5 GY 6/8) and moderate yellow green (2.5 GY 5/6) (2.5 GY 6/6) (5 GY 5/6). (b) Marginal blade area — Pale yellow green (5 GY 9/2) (2.5 GY 9/2) and greenish white (5 GY 9/1). (c) Basal area — Pale yellow green (2.5 GY 9/2) (5 GY 8.5/2) and light yellow green (2.5 GY 9/4) (5 GY 9/4).

III. *Corymb.*—A. Primary Inflorescence branches — (1) Number: No. 1: 4. No. 2: 3. No. 3: 3. No. 4: 2. (2) Primary branch sizes: (a) Lengths — No. 1: 10, 53, 10 and 30 mm respectively. No. 2: 30, 20 and 35 respectively. No. 3: 25, 20 and 25 respectively. No. 4: 48 and 20 respectively. (b) Diameters — 3–5 mm intermediate the proximal and distal ends. (3) Primary branch color (at anthesis): Dark yellowish green (10 GY 4/4), moderate yellowish green (10 GY 5/6), moderate yellow green (7.5 GY 5/6) and strong yellow green (5 GY 5/8). B. Primary inflorescence bracts — (1) Number of bracts: One (1) subtending each primary branch with two (2) of twelve (12) primary branches having one (1) non-subtending bract intermediate proximal and distal ends of the branch. (2) Primary bract sizes (flowering inflorescences with live bracts): (a) Length — No. 3: 35, 25 and 10 (non-subtending bract) mm. No. 4: 32 and 22 (non-subtending bract) mm. (b) Width (maximum) — No. 3: 13, 8 and 7 (non-subtending bract) mm. No. 4: 13, 7 (non-subtending bract) mm. (3) Primary bract color (at anthesis): (a) Center field area — Moderate yellow green (2.5 GY 5/6) (5 GY 5/6) and strong yellow green (5 GY 5/8) (5 GY 6/8). (b) Marginal area — Pale yellow green (2.5 GY 8.5/2) (5 GY 8.5/2) and greenish white (5 GY 9/10). (c) Basal area — Pale yellow green (5 GY 8/2) (5 GY 8.5/2) and yellow green (2.5 GY 9/4) (5 GY 9/4). C. Secondary inflorescence branches — (1) Number of secondary branches: No. 1: 6. No. 2: 2. No. 3: 2. No. 4: 1. (2) Secondary branch sizes: (a) Lengths — No. 1: 15, 15, 9. 12 and 10 mm respectively. No. 2: 30 and 20 mm respectively. No. 3: 25 and 13 mm respectively. No. 4: 26 mm. (b) Diameters — 2–4 mm intermediate the proximal and distal ends. (3) Secondary branch color (at anthesis): Dark yellowish green (10 GY 4/4), moderate yellowish green (10 GY 5/6), moderate yellow green (7.5 GY 5/6) (7.5 GY 5/4) and strong yellow green (5 GY 5/8). D. Secondary inflorescence bracts — (1) Number of secondary inflorescence bracts: One (1) subtending each secondary branch and with one (1) of eleven (11) secondary branches having one (1) non-subtending bract intermediate the proximal and distal ends of the branch. (2) Secondary inflorescence bract sizes (flowering inflorescences with live bracts): (a) Lengths — No. 3: 25 and 11 (non-subtending bract) mm respectively. No. 4: 17 mm (b) Widths — No. 3: 8 and 5 (non-subtending bract) mm respectively. No. 4: 7 mm. (3) Secondary inflorescence bract color (at anthesis): (a) Center blade area — Light yellow green (5 GY 8/6) (5 GY 8.5/6), moderate yellow green (5 GY 5/6) (%6/6), strong yellow green (5 GY 5/8) (5 GY 6/8) and brilliant yellow green (5 GY 8.5/8). (b) Marginal area — Pale yellow green (5 GY 8.5/2) (5 GY 9/2) and greenish white (5 GY 9/1). (c) Basal area — Pale yellow green (5 GY 8/2) (5 GY 8.5/2) and light yellow green (2.5 GY 8.5/6) (5 GY 8/6). E. Tertiary inflorescence branches — (1) Number of tertiary inflorescence branches: No. 1: 5. No. 2: 3. No. 3: 2. No. 4: 0. (2) Tertiary inflorescence branch sizes: (a) Lengths — No. 1: 15, 11, 10, 5 and 9 mm respectively. No. 2: 5, 5 and 10 respectively. No. 3: 8 and 12 mm respectively. No. 4: 0. (b) Diameter (maximum) — 2–4 mm intermediate the proximal and distal ends. (3) Tertiary inflorescence branch color (at anthesis): Dark yellowish green (10 GY 4/4), moderate yellowish green (10 GY 5/6), moderate yellow green (7.5 GY 5/6) (7.5 GY 5/4) and strong yellow green (5 GY 5/8). F. Tertiary inflorescence bracts — (1) Number of tertiary inflorescence bracts: One (1) subtending each tertiary branch. (2) Tertiary inflorescence bract sizes (flowering inflorescences with live bracts): (a) Lengths — No. 3: 10 and 12 mm respectively. No. 4: 0. (b) Widths — No. 3: 5 and 4 mm respectively. No. 4: 0. (3) Tertiary inflorescence bract color (at anthesis): (a) Center blade area — Light yellow green (5 GY 8/6) (5 GY 8.5/6), moderate yellow green (5 GY 5/6) (5 GY 6/6), strong yellow green (5 GY 5/8) (5 GY 6/8) and brilliant yellow green (5 GY 8.5/8). (b) Marginal area — Pale yellow green (5 GY 8.5/2) (5 GY 9/2) and greenish white (5 GY 9/1). (c) Basal area — Pale yellow green (5 GY 8/2) (5 GY 8.5/2) and light yellow green (2.5 GY 8.5/6) (5 GY 8/6). G. Pedicels — (1) Number of pedicels: No. 1: 21. No. 2: 10. No. 3: 10. No. 4: 6. (2) Pedicel sizes — (a) Lengths — 7–10 mm from the subtending bract. (b) Diameter — 2.5–3.0 mm intermediate the proximal and distal ends and 3.0–4.5 mm at the distal ends. (3) Pedicel color (at anthesis): Moderate yellowish green (10 GY 5/4) (10 GY 5/6), dark yellowish green (10 GY 4/4) (2.5 G 4/4) (2.5 G 4/6) and moderate green (5 G 4/6). H. Flowers — (1) Sepals (at anthesis): (a) Sepal sizes — 1. Length: 110–115 in the free portion of the calyx. 2. Width (maximum): 38–40 mm. (b) Sepal color — 1. Distal area (distal ⅔ of free sepal): Pale greenish yellow (10 Y 9/4) (7.5 Y 9/4), light greenish yellow (10 Y 9/6) (7.5 Y 9/6) (near 10 Y 8/8), strong greenish yellow (near 10 Y 8/8) and brilliant greenish yellow (near 10 Y 8/8) (near 7.5 Y 9/8). 2. Basal area (proximal ⅓ of free sepal): a. Medial field — Light yellow green (2.5 GY 8.5/6) (5 GY 8.5/6) and brilliant yellow green (2.5 GY 8.5/8) (2.5 GY 8/8). b. Marginal area — Pale yellow green (10 Y 9/2) (2.5 Y 9/2), pale yellow (near 7.5 Y 9/2) (near 5 Y 9/2) and yellowish white (near 7.5 Y 9/2) (near 5 Y 9/2). (2) Petals (at anthesis): (a) Petal size — 1. Length: 105–110 mm in the free portion of the corolla. 2. Width (maximum): 56–62 mm in the free portion of the corolla. (b) Petal color — 1. Distal area (distal ⅔ of free petal). a. Basic field — Pale greenish yellow (7.5 Y 9/4) (10 Y 9/4), light greenish yellow (7.5 Y 9/6) (10 Y 9/6) and brilliant greenish yellow (10 Y 0/10). b. Axial stripe — Pale yellow green (10 Y 9/2) and pale greenish yellow (10 Y 9/4). 2. Basal area (proximal ⅓ of the free petal): a. Medial field — Light greenish yellow (10 Y 8.5/6) (near 10 Y 8.5/8), brilliant greenish yellow (near 10 Y 8.5/8) (10 Y 8.5/10), brilliant yellow green (2.5 GY 8/8) (2.5 GY 9/8) and strong yellow green (2.5 GY 9/4). b. Marginal area — Pale greenish yellow (10 Y 9/4), pale yellow green (10 Y 9/2) (2.5 GY 9/2) and light yellow green (2.5 GY 9/4). (3) Perianth tube (at anthesis): (a) Perianth tube size — (1) Length: 23–27 mm. (2) Diameter (outside): 6–7 mm intermediate the proximal and distal ends. (3) Diameter (inside): 2.5–3.5 mm intermediate the proximal and distal ends. (b) Perianth tube color — Brilliant yellow green (2.5 GY 8/10) (2.5 GY 8/8) and strong yellow green (2.5 GY 7/8) (2.5 GY 7/10). (4) Stamens (at anthesis): (a) Filaments — 1. Filament sizes: a. Lengths — 62–72 mm. b. Diameters — about 3 mm at the proximal ends and about 1.5 mm at the distal ends. 2. Filament color: Brilliant greenish yellow (10 Y 8.5/10) proximally and merging distally to light greenish yellow (7.5 Y 9/6). (b) Anthers — 1. Anther sizes: a. Lengths — 10–12 mm. b. Diameter (maximum) — 2–3 mm. 2. Anther color: a. Anther connective — Pale yellowish pink (near 2.5 YR 8/2) (near 5 YR 8/2), grayish yellowish pink (near 2.5 YR 8/2) (near 5 YR 8/2), brownish pink (near 5 YR 8/2), light yellowish pink (near 2.5 YR 8/4), and moderate yellowish pink (near 2.5 YR 8/4). b. Pollen (open anther) — Light orange yellow (near 7.5 YR 8/10), moderate orange yellow (near 7.5 YR 8/10), strong orange yellow (7.5 YR 7/12) (10 YR 7/12) (near 7.5 YR 8/10), and brilliant orange yellow (near 7.5 YR 8/10). (5) Pistil (at anthesis): (a) Ovary — 1. Sizes: a. Heights: 4–6 mm. b. Diameters: 3–4 mm. c. Ovule diameter (maximum): 0.2–0.3 mm. 2. Ovary color: Light yellow green (2.5 YG 8.5/6), strong yellow green (2.5 GY 7/8) (2.5 GY 7/10) (5 GY 7/8) (5 GY 7/10) and brilliant yellow green (2.5 GY 8.5/8) (5 GY 8/8). Ovules-yellowish white (10 Y 9/1). (b) Style — 1. Style sizes: a. Lengths — 125–140 mm. b. Diameters — 1.4–1.7 mm intermediate the proximal and distal ends. 2. Style color: Pale greenish yellow (10 Y 9/4), light greenish yellow (10 Y 8.5/6), pale yellow (near 7.5 Y 9/2) and yellowish white (near 7.5 Y 9/2). (c) Stigma — 1. Stigma sizes: a. Thickness: about 0.3 mm. b. Diameters: about 1 mm. 2. Stigma color: Pale yellow (near 7.5 Y 9/2) and yellowish white (near 7.5 Y 9/2).

I claim:

1. The new plant variety of the Lily family substantially as shown and described herein.

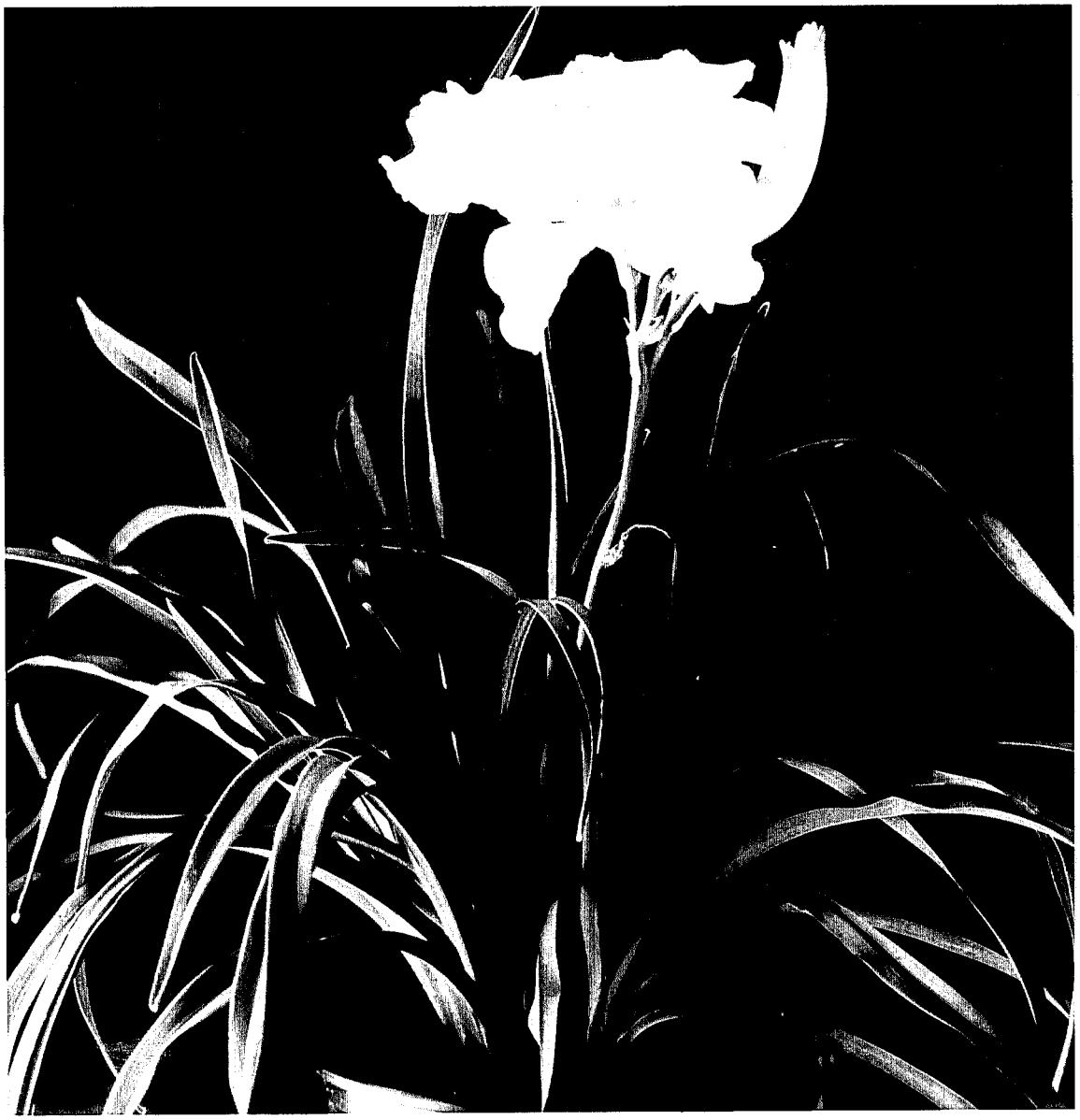

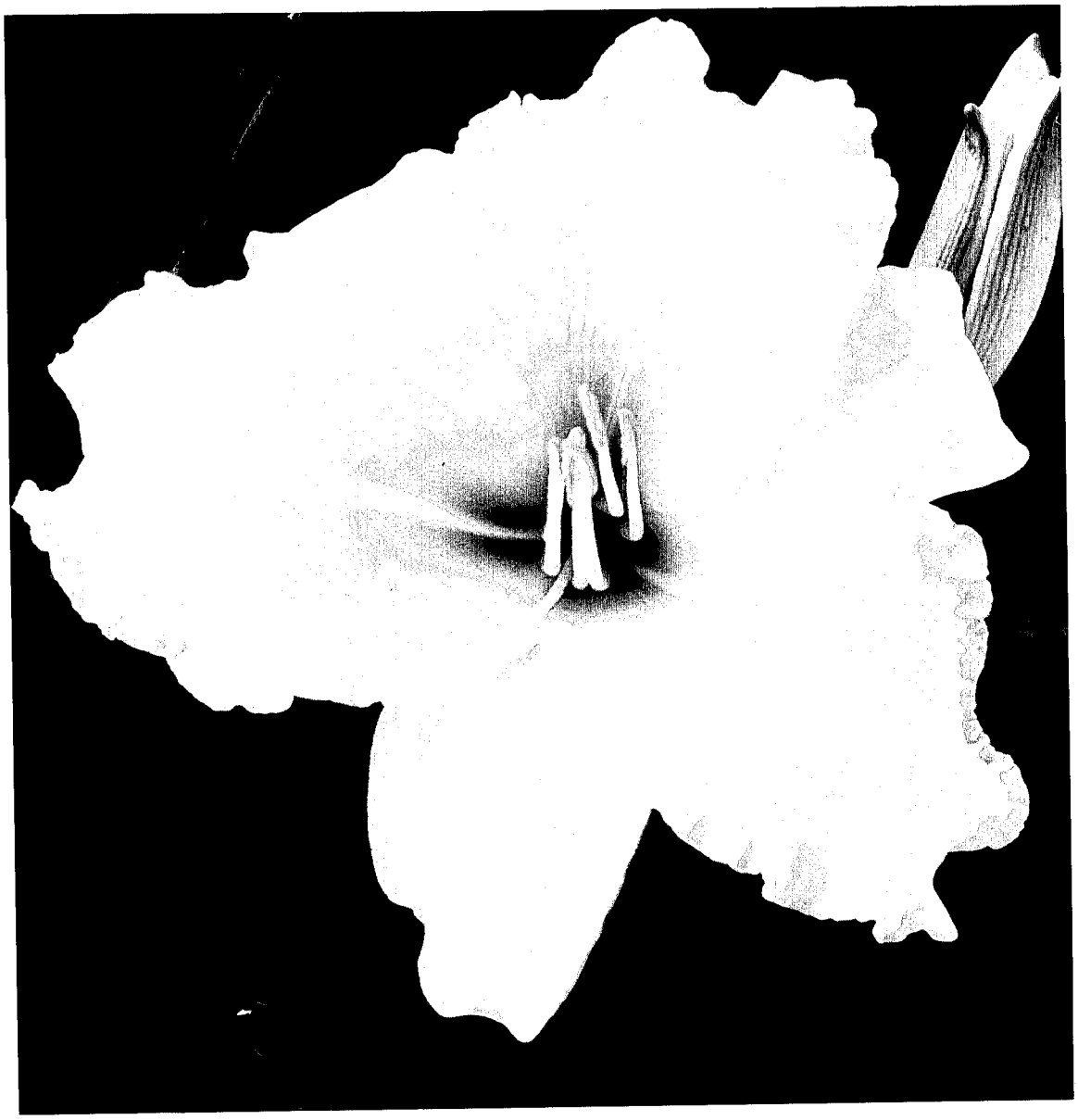

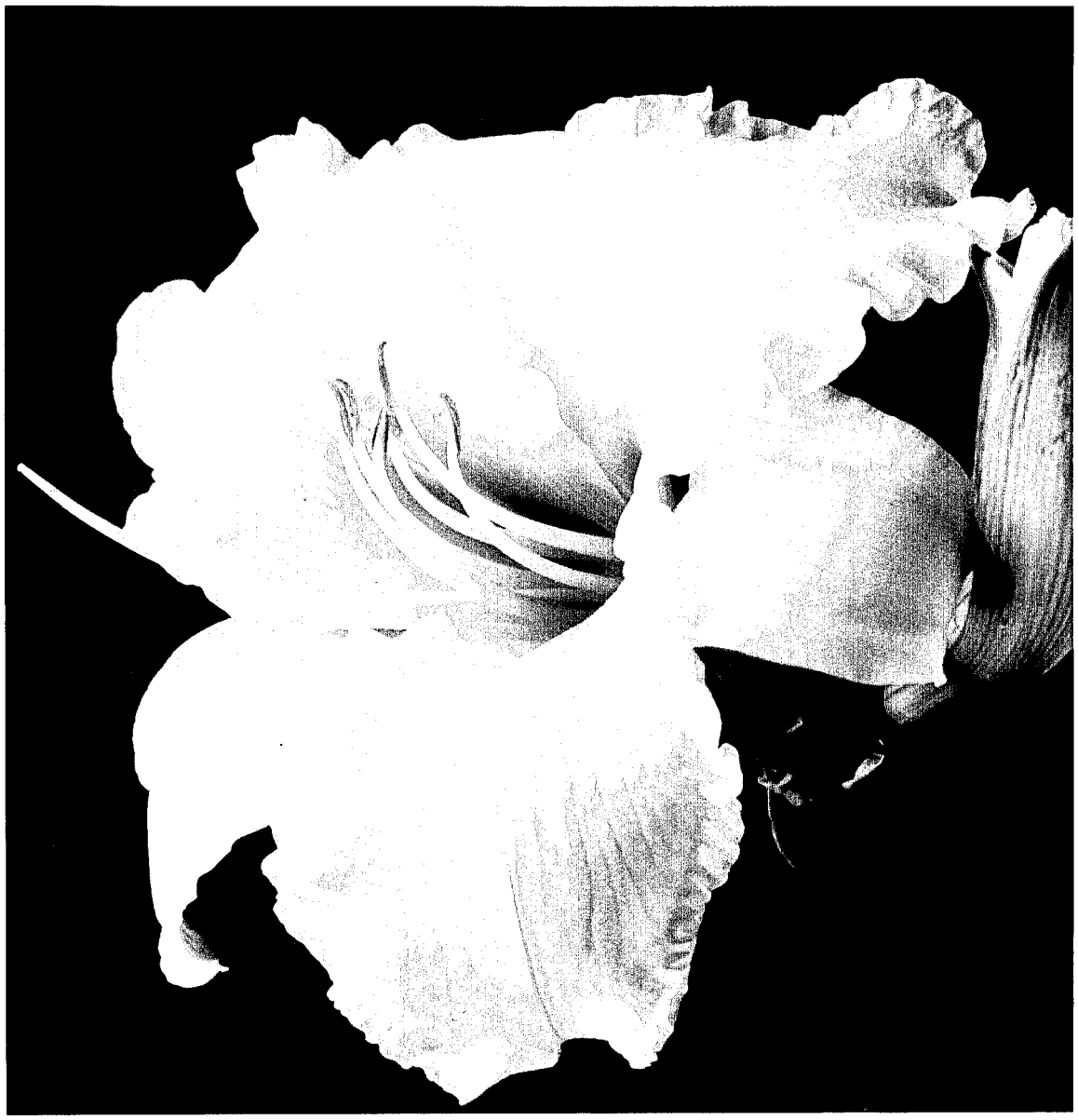

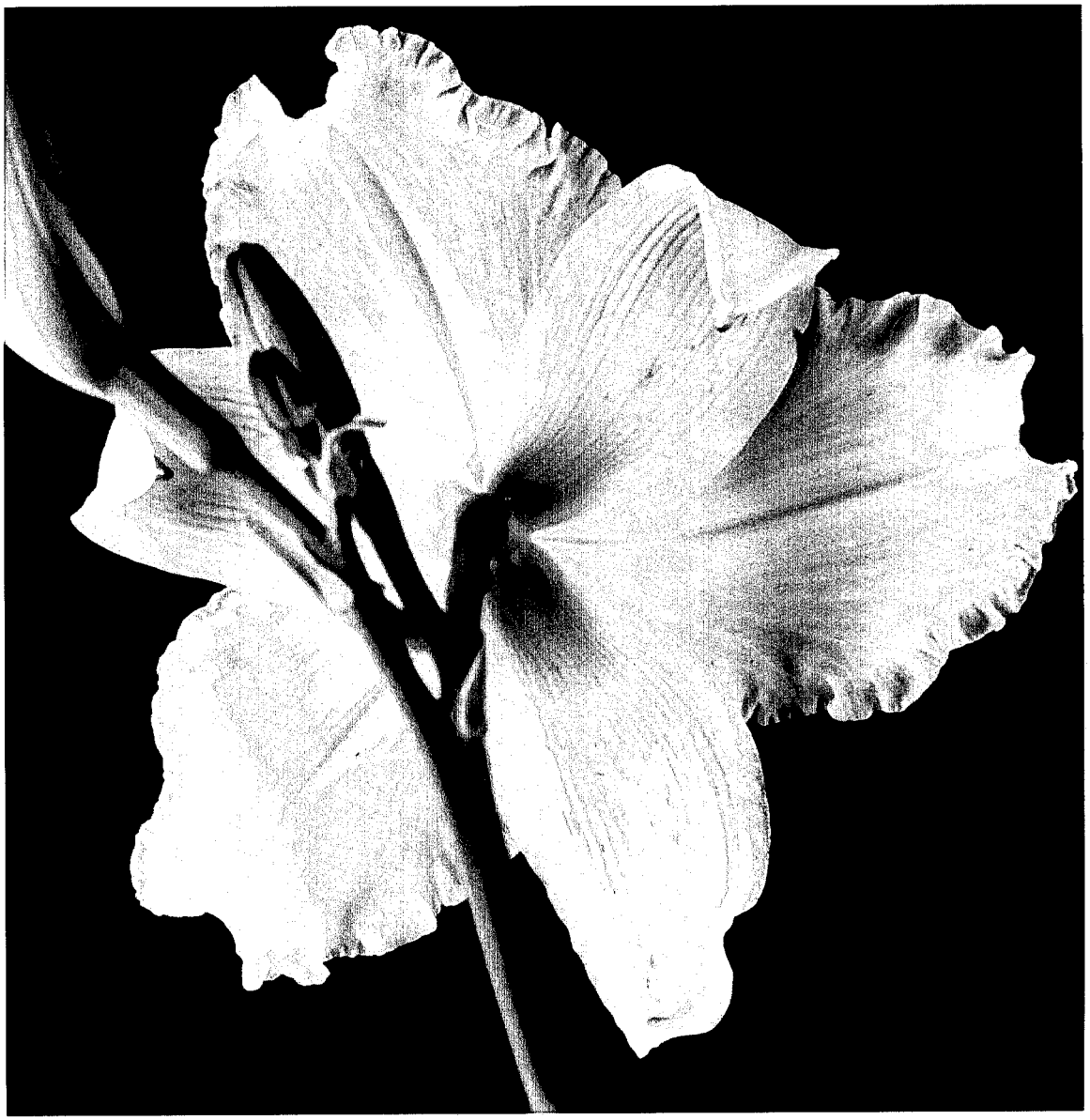

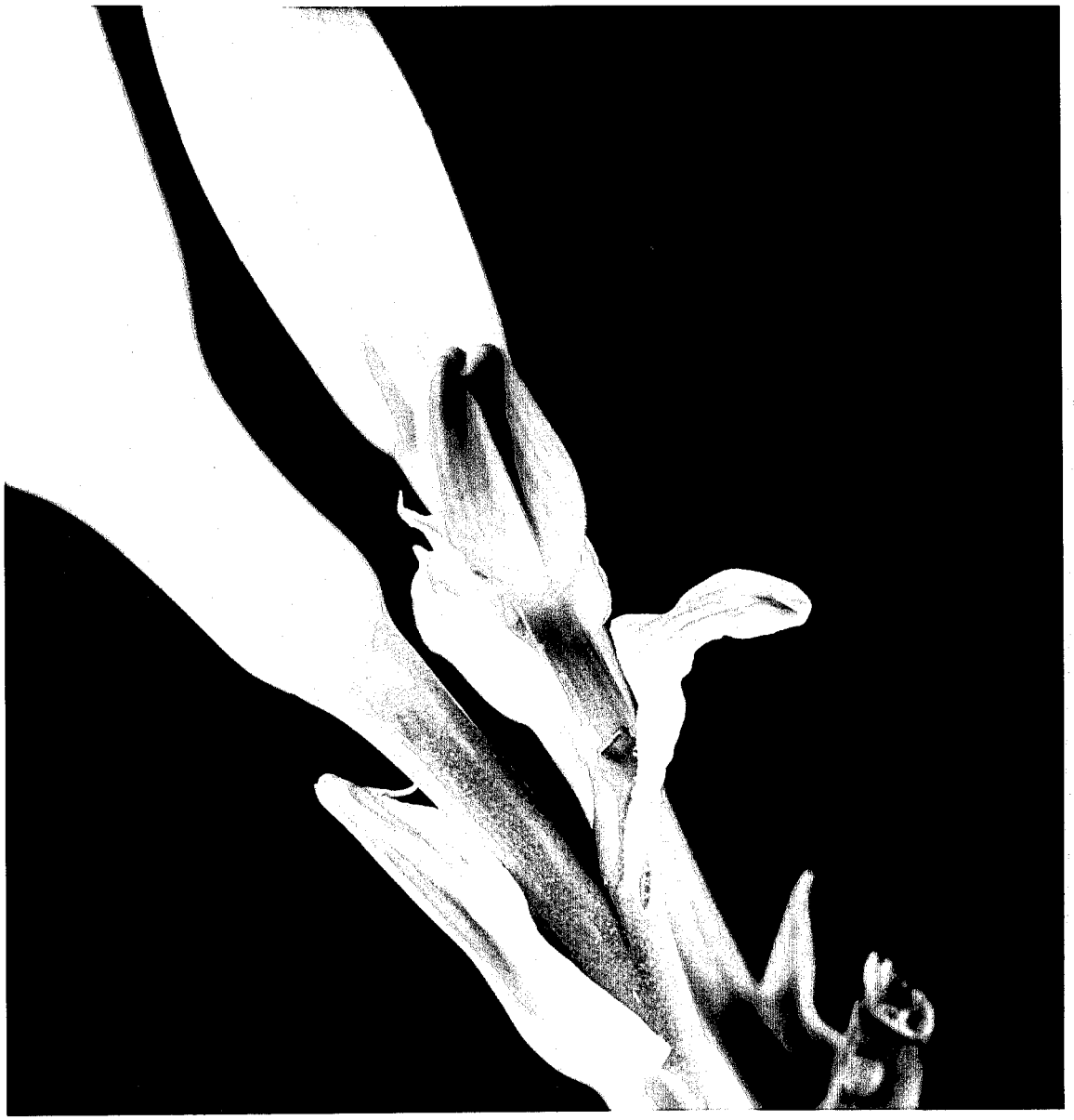

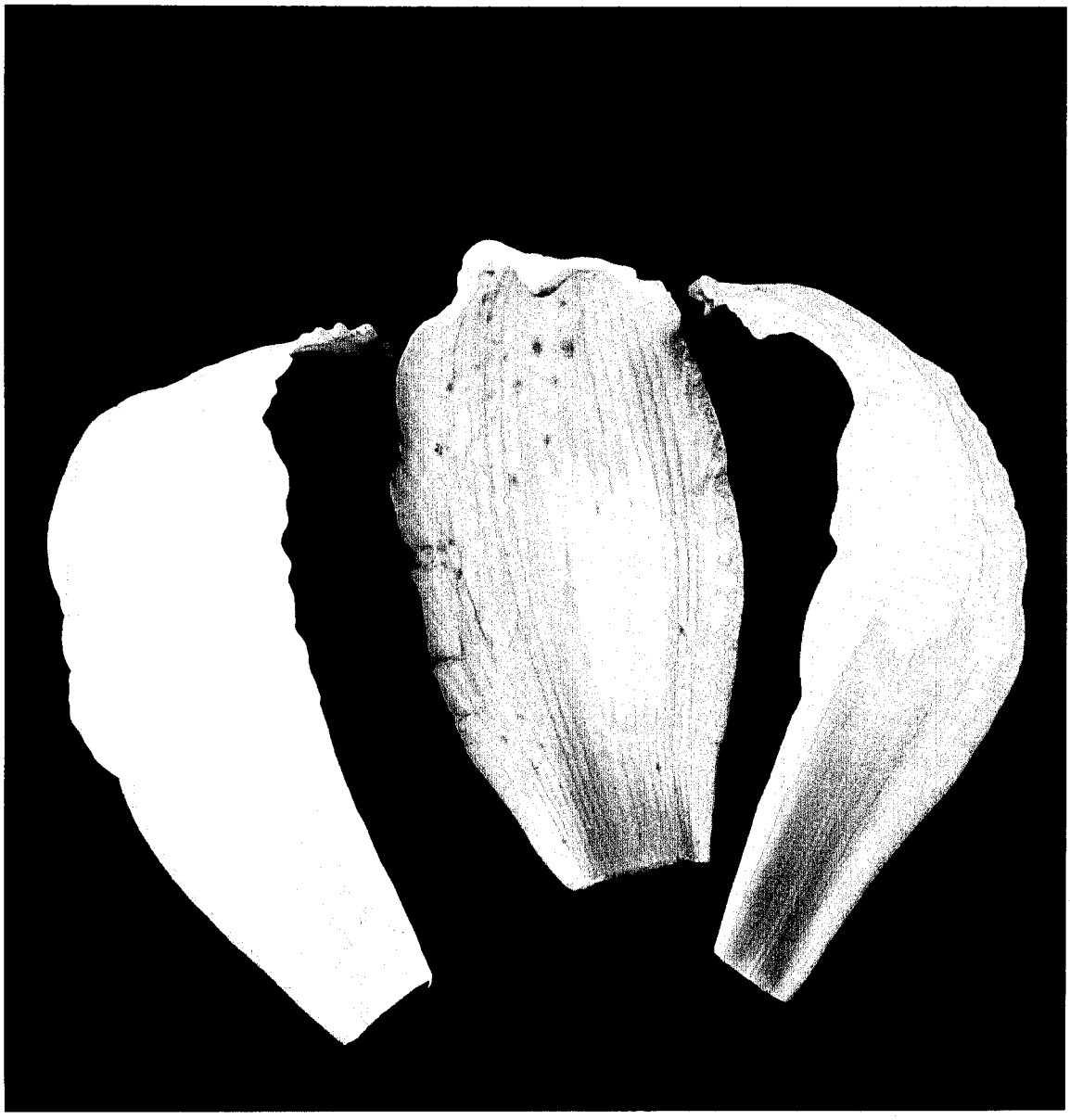

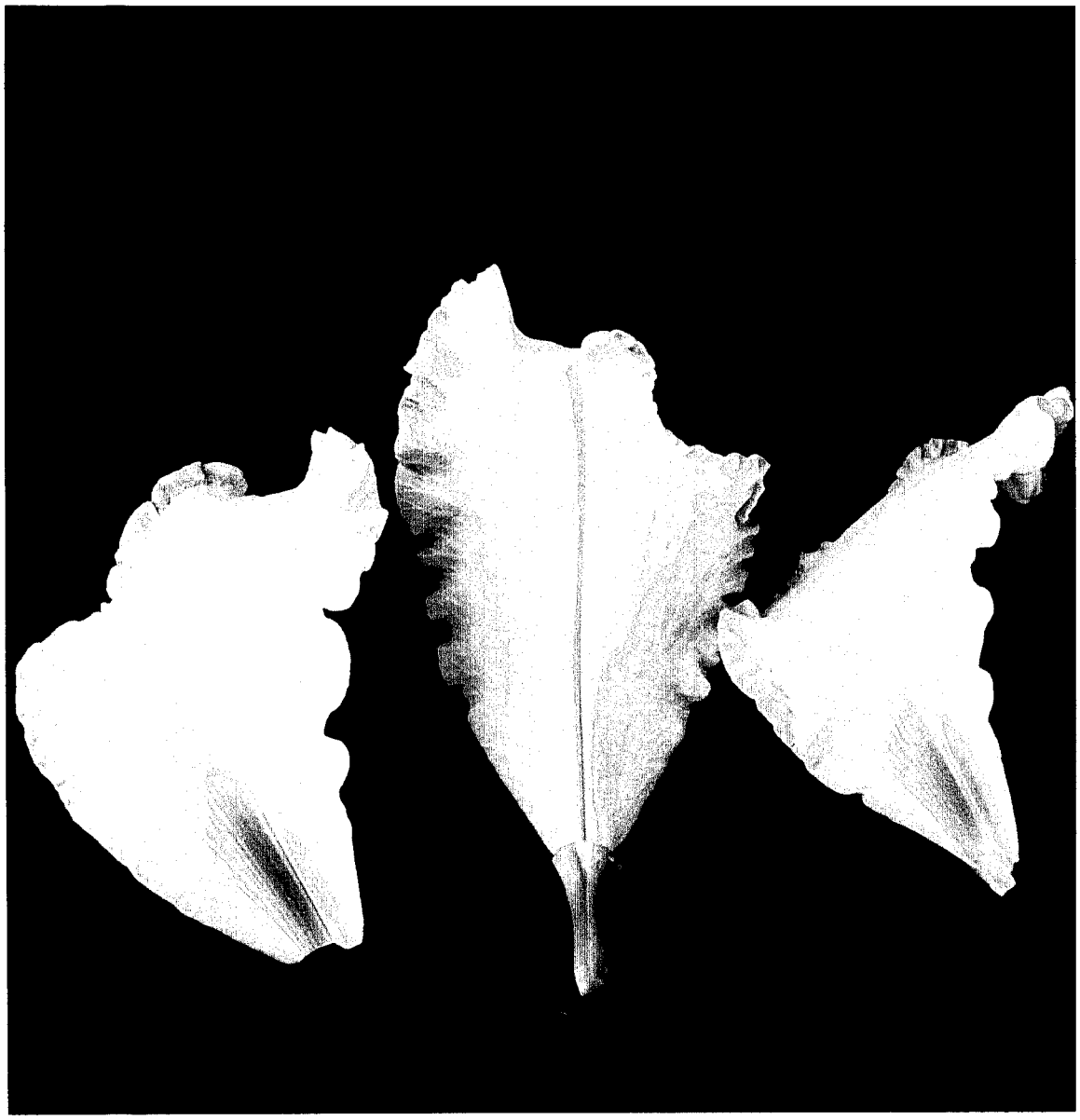

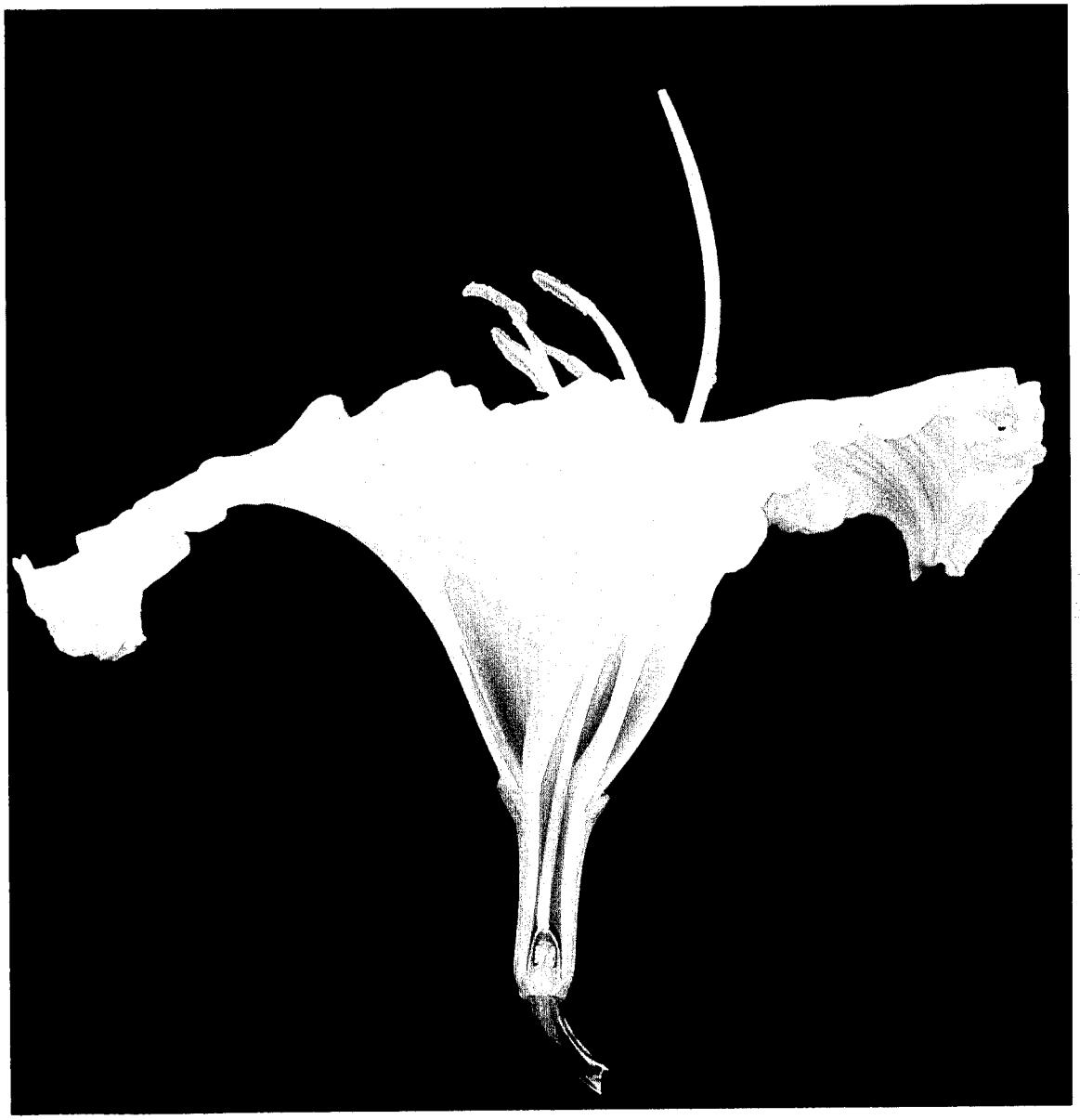

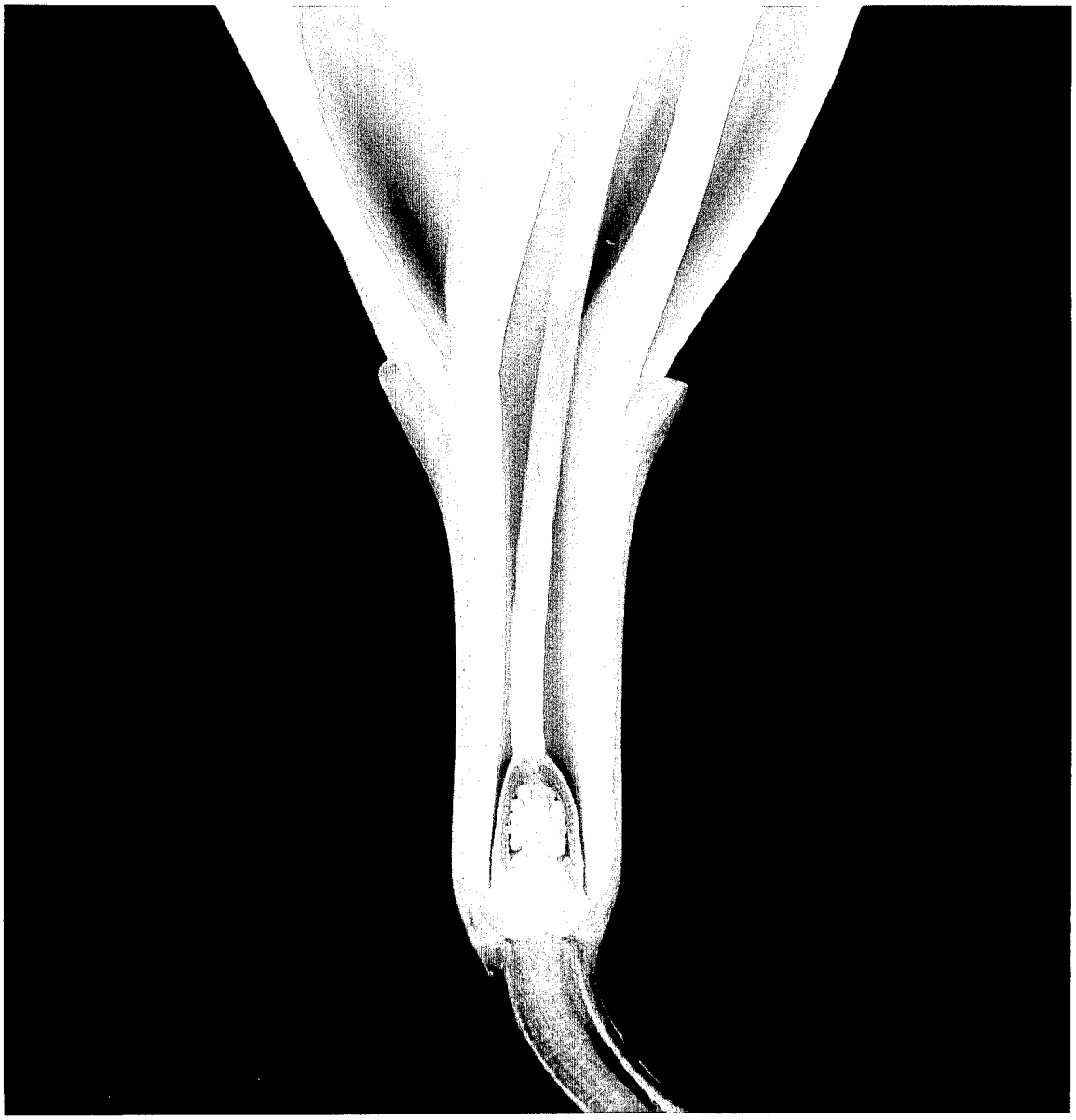

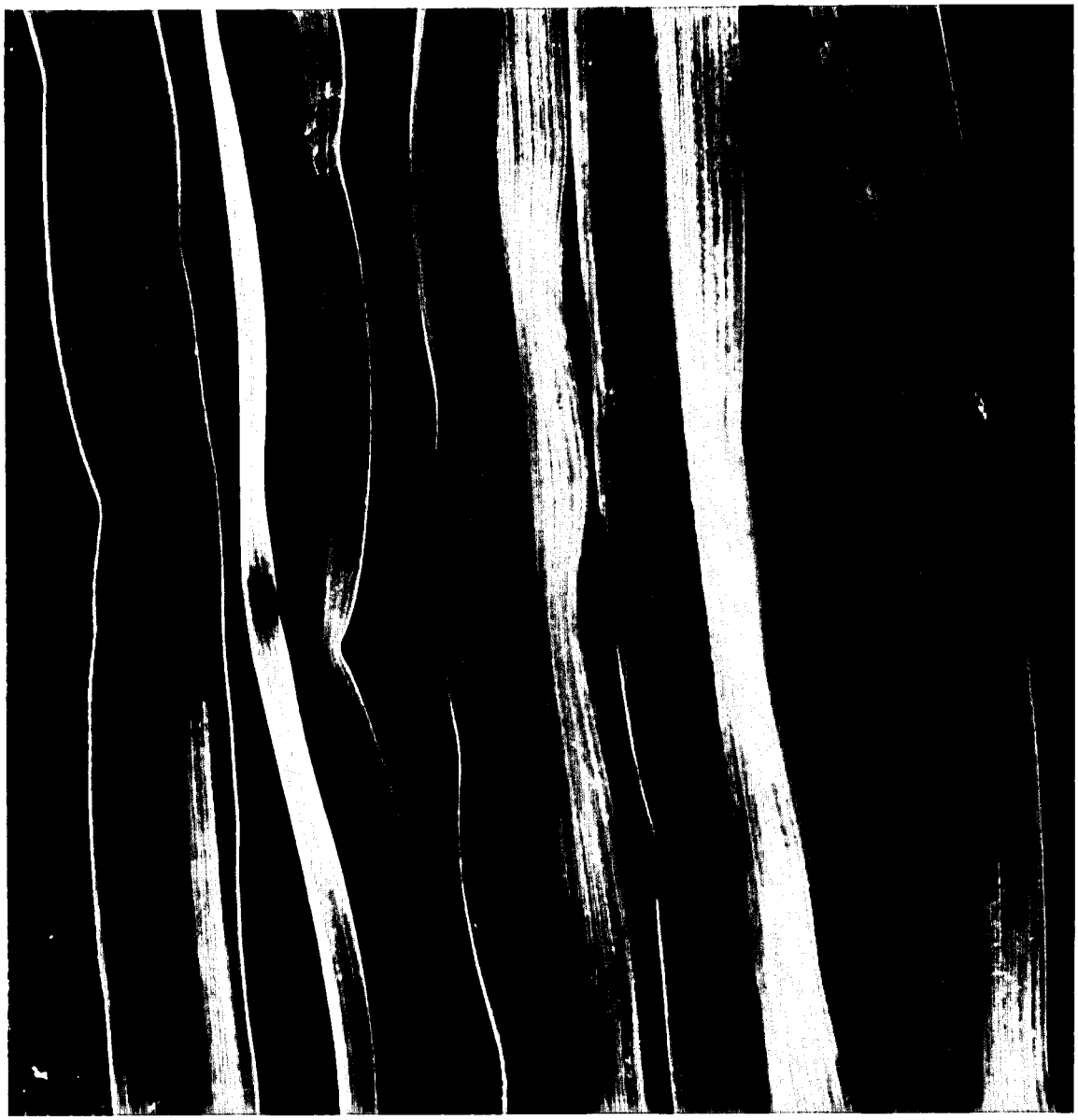

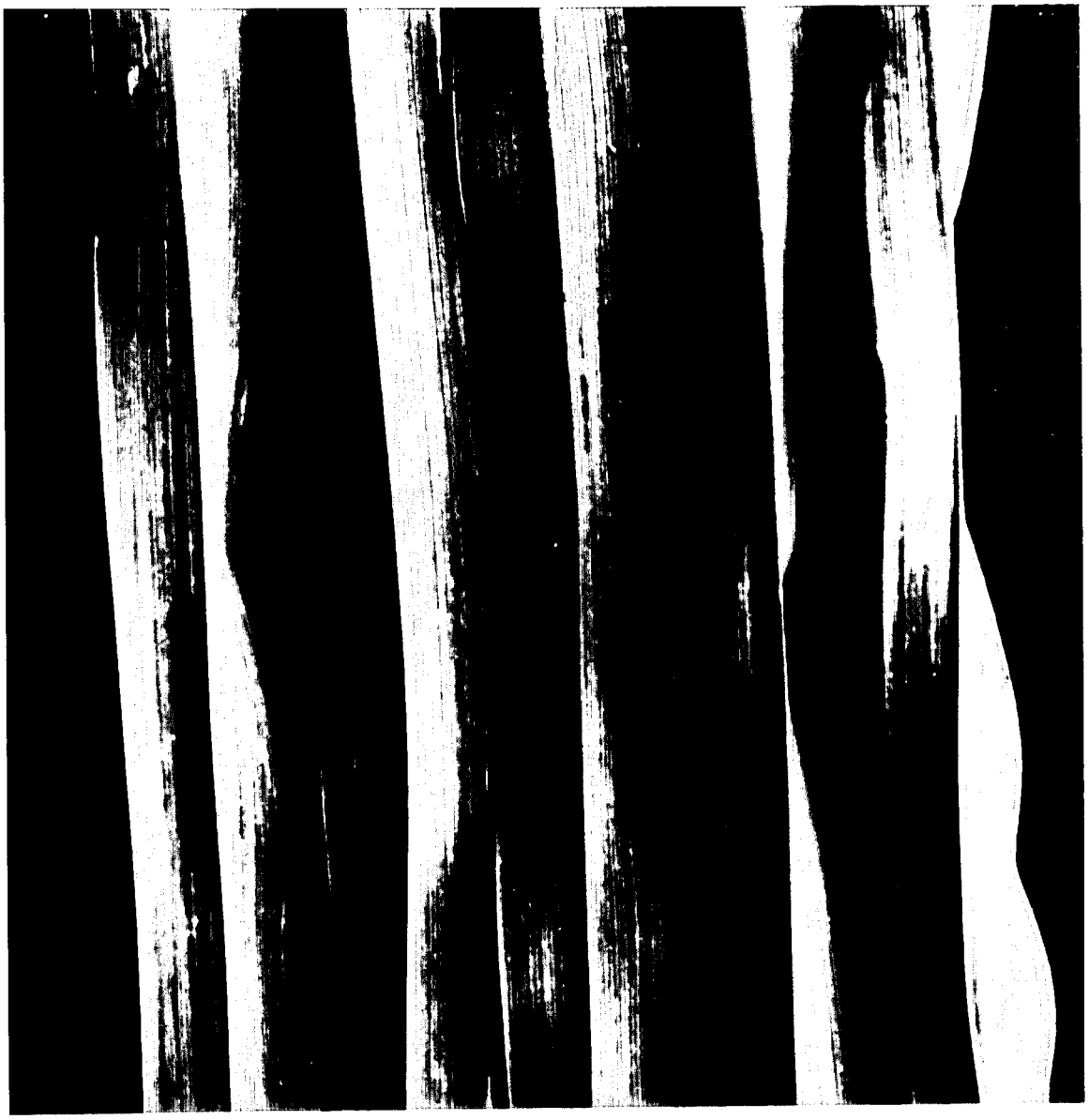

* * * * *